United States Patent
Ikai et al.

(10) Patent No.: US 6,949,684 B2
(45) Date of Patent: Sep. 27, 2005

(54) PROCESS FOR PREPARING 1,2,4-BUTANETRIOL

(75) Inventors: Kousei Ikai, Amagasaki (JP); Masafumi Mikami, Amagasaki (JP); Yoshiro Furukawa, Amagasaki (JP); Takeshi Urano, Amagasaki (JP); Seiji Ohtaka, Amagasaki (JP)

(73) Assignee: Daiso Co., Ltd., Osaka (JP)

( * ) Notice: Subject to any disclaimer, the term of this patent is extended or adjusted under 35 U.S.C. 154(b) by 576 days.

(21) Appl. No.: 10/189,804

(22) Filed: Jul. 8, 2002

(65) Prior Publication Data

US 2003/0045759 A1 Mar. 6, 2003

Related U.S. Application Data

(63) Continuation-in-part of application No. 09/623,201, filed as application No. PCT/JP99/00867 on Feb. 25, 1999, now abandoned.

(30) Foreign Application Priority Data

Mar. 3, 1998 (JP) ............................................. 10-50723

(51) Int. Cl.$^7$ .................... C07C 31/22; C07C 31/18; C07C 29/147; C07C 29/136
(52) U.S. Cl. ..................................... 568/853; 568/864
(58) Field of Search ................................ 568/853, 864

(56) References Cited

U.S. PATENT DOCUMENTS

| | | | |
|---|---|---|---|
| 2,683,721 A | 7/1954 | Schlesinger | 260/343.3 |
| 4,410,744 A | 10/1983 | Campbell et al. | 568/864 |
| 5,196,601 A | 3/1993 | Kitsuki et al. | 268/817 |
| 5,808,107 A | 9/1998 | Hollingsworth | 549/323 |

FOREIGN PATENT DOCUMENTS

| | | |
|---|---|---|
| JP | 64-68366 | 3/1989 |
| WO | WO 98/08793 | 3/1998 |
| WO | WO 99-23086 | 5/1999 |

OTHER PUBLICATIONS

Shibata et al.; "Synthesis of Optically Active 3–Mercaptopyrrolidine Derivatives, Synthetic Intermediates of Carbapenem RS0533 and its Isomer"; Heterocycles, 1986, vol. 24, No. 5, pp. 1331–1346.

MacNiel et al.; "Asymetric Synthesis, Asymmetric Catalytic Hydrogenation Using Chiral Chelating Six–Membered Ring Diphosphines," J. Amer. Chem. Soc., 1981, vol. 103, No. 9, pp 2273–2280.

Pawlak et al.; Stereochemical Studies of Polyols from the Polyene Macrolide Lienomycin,; J. Org. Chem., 1987, vol. 52, No. 13, pp. 2896–2901.

Tsuri et al.; "An Efficient and Stereocontrolled Synthesis of Platelet Activating Factor from (S)–(–)–Malic Acid," Tetrahedron Lett., 1985, vol. 26, No. 42, pp. 5195–5198.

Tandon et al.; "Sythesis of Enantiomerically Pure (S)–(+)–3–Hydroxytetrahydrofuran and its R Enantiomer from Malic or Tartaric Acid,"J. Org. Chem., 1983, vol. 48, No. 16, pp. 2767–2769.

Robert C. Corcoran; "Chelation and Non–Chelation Deirecte Cleavage of Acetals," Tetrahderon Lett., 1990, vol. 31, No. 15, pp. 2101–2104.

J.E.G. Barnett et al.; "Fluorocarbohydrates. Part VI* Selective Reductionof Oxo–esters by Potassium Borohydride," J. Chem. Soc., 1963, pp. 2743–2747.

M. Thiam et al.; "Malic Acid as Chiral Synthon: Synthesis of 1,2 and 1,3 Optically Active Diols" Synthetic Communications, vol. 22, No. 1, 1992; pp. 83–95: XP000984435.

*Primary Examiner*—Elvis O. Price
(74) *Attorney, Agent, or Firm*—Armstrong, Kratz, Quintos, Hanson & Brooks, LLP

(57) ABSTRACT

An object of the present invention is to provide a process wherein 1,2,4-butanetriol can be obtained safely, easily and inexpensively without causing problems concerning wastewater. A malic diester, 3-hydroxy-γ-butyrolactone or 3,4-dihydroxybutanoate represented by the following formulae (I), or a mixture thereof is reduced with sodium borohydride in an organic solvent to give 1,2,4-butanetriol represented by the following formula (II). When an optically active substance is used as the above-mentioned starting compound, substantially no recemization occurs during the reduction, and optically active 1,2,4-butanetriol is obtained.

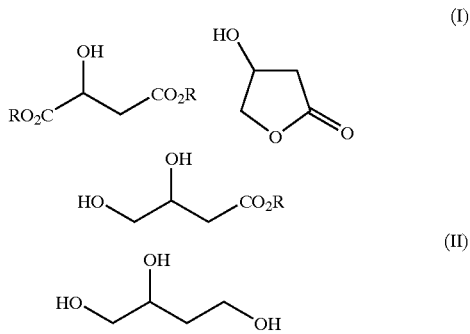

23 Claims, No Drawings

PROCESS FOR PREPARING 1,2,4-BUTANETRIOL

This application is a continuation-in-part application of the U.S. patent application Ser. No. 09/623,201 filed Aug. 29, 2000 now abandoned based on International Application PCT/JP99/00867 filed Feb. 25, 1999.

TECHNICAL FIELD

The present invention relates to a process for preparing 1,2,4-butanetriol, particularly optically active 1,2,4-butanetriol, which is a useful compound as a synthetic intermediate of medicines, agricultural chemicals and the like.

BACKGROUND ART 1,2,4-Butanetriol is an industrially useful compound which has been known from old times, and it has been used as a synthetic precursor of 3-hydroxytetrahydrofuran and 3-hydroxypyrrolidine derivatives and the like. There have been reported three conventional processes for preparing this compound by the following processes: 1) a process for reducing dimethyl malate with lithium aluminum hydride (J. Amer. Chem. Soc., 103, 9, 2273–2280 (1981)), 2) a process for reducing dimethyl malate with sodium borohydride in a mixed solvent of THF/H$_2$O (J. Org. Chem., 52, 13, 2896–2901 (1987)) and 3) a process for reducing malic acid with a borane-dimethyl sulfide complex in THF (Tetrahedron Lett., 26, 42, 5195–5198 (1985)).

However, the above-mentioned conventional processes had the following problems. First, in the process 1), lithium aluminum hydride, which is difficult to handle industrially and expensive, has to be used as a reducing agent. When an optically active substance is used as the starting material, it is difficult to obtain a target product having a high optical purity, since racemization proceeds during the reaction (J. Org. Chem., 48, 16, 2767–2769 (1983)). Accordingly, it is necessary to carry out troublesome steps wherein a hydroxyl group is protected and then ester groups are reduced to give an optically active target product through deprotection, or a reduced product is converted into its derivative and then the derivative is recrystallized to raise its optical purity. In the process 2), since THF is used as the solvent, it is feared that THF produces a peroxide and the peroxide explodes when THF is concentrated. Accordingly, this process is difficult to apply to industry. In addition, since drain is contaminated by THF to give wastewater and wastewater treatment is necessary, this process has many problems in practice. In the process 3), since dimethyl sulfide gives out a bad smell and it is expensive, it is industrially difficult to use the borane-dimethyl sulfide complex. Since THF is used as the solvent, the above-mentioned fear and wastewater problems are unavoidable.

For these reasons, an economically inexpensive process for obtaining 1,2,4-butanetriol, which is a useful compound as a synthetic intermediate of medicines, agricultural chemicals and the like, by using an easily available compound as a starting material has been desired.

An object of the present invention is to provide a process wherein 1,2,4-butanetriol can be obtained safely, easily and inexpensively without causing the problems concerning wastewater.

DISCLOSURE OF THE INVENTION

Studying in order to solve the above-mentioned problems, the present inventors found that desired 1,2,4-butanetriol can be prepared inexpensively by using a malic diester, 3-hydroxy-γ-butyrolactone or a 3,4-dihydroxybutanoate as a starting compound and by reducing this compound with a specific reducing agent, and completed the present invention.

The present inventors also found that substantially no recemization occurs during the reduction and optically active 1,2,4-butanetriol is obtained when an optically active substance is used as the above-mentioned starting compound.

A first process according to the present invention is a process for preparing 1,2,4-butanetriol characterized in that a malic diester, 3-hydroxy-γ-butyrolactone or a 3,4-dihydroxybutanoate represented by the following formulae (I), or a mixture thereof is reduced with sodium borohydride in an organic solvent to give 1,2,4-butanetriol represented by the following formula (II).

A second process according to the present invention is a process for preparing 1,2,4-butanetriol characterized in that a malic diester, 3-hydroxy-γ-butyrolactone or a 3,4-dihydroxybutanoate represented by the following formulae (I), or a mixture thereof is reduced with a boronic reducing agent represented by the general formula M(BH$_4$)$_n$ (wherein "M" is a metal atom other than sodium, and "n" is an integer which is equal to a valence of the metal M) in an organic solvent to give 1,2,4-butanetriol represented by the following formula (II).

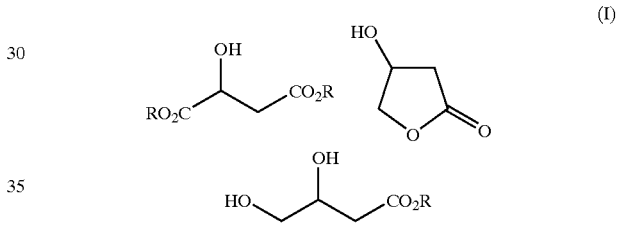

(wherein "R" is an alkyl group having four carbon atoms or fewer)

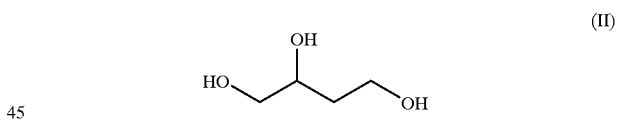

When the malic diester, 3-hydroxy-γ-butyrolactone and the 3,4-dihydroxybutanoate to be used as the starting materials of the first and second processes are racemates (I), the obtained 1,2,4-butanetriol is also a racemate (II). The above-mentioned three starting compounds can be used individually or in combination.

The malic diester, 3-hydroxy-γ-butyrolactone or the 3,4-dihydroxybutanoate to be used as the starting material can be a compound obtained by any methods. The malate can be obtained, for example, according to Tetrahedron Lett., 33, 11, 1415–1418 (1992). 3-Hydroxy-γ-butyrolactone and the 3,4-dihydroxybutanoate can be obtained, for example, by the method described in Japanese Laid-open Patent Publication No. 47296/1997.

The alkyl group R of the malic diester or the 3,4-dihydroxybutanoate is not limited to particular groups so far as the alkyl group has four carbon atoms or fewer. Preferred alkyl group is a methyl group or an ethyl group in terms of reactivity of the reduction.

The malic diester, 3-hydroxy-γ-butyrolactone and the 3,4-dihydroxybutanoate to be used as the starting materials of the first and second processes can be optically active substances represented by the following formulae (III). In this case, substantially no recemization occurs during the reduction, and the obtained 1,2,4-butanetriol is an optically active substance represented by the following formula (IV). In this reaction, the above-mentioned three optically active starting compounds can also be used individually or in combination, and optically active 1,2,4-butanetriol is obtained in either case.

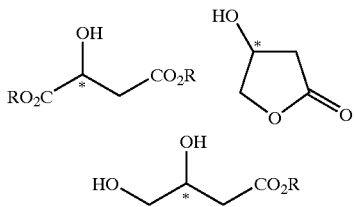

(III)

(wherein "R" is an alkyl group having four carbon atoms or fewer)

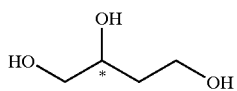

(IV)

When the optically active substance is prepared, the optically active malic diester, optically active 3-hydroxy-γ-butyrolactone and the optically active 3,4-dihydroxybutanoate which are the starting materials can also be obtained by the methods described in the above-mentioned literatures. The alkyl group R of the optically active malic diester or 3,4-dihydroxybutanoate can also be a group having four carbon atoms or fewer. Preferred alkyl group is a methyl group or an ethyl group in terms of reactivity of the reduction.

In the first process, preferred organic solvents are alcohols or mixed solvents containing an alcohol. Preferred alcohols are aliphatic alcohols having three carbon atoms or fewer in terms of solubility of sodium borohydride. Examples of the alcohol are methanol, ethanol, propanol, isopropanol, ethylene glycol and propylene glycol. Methanol, ethanol and ethylene glycol are more preferable among them. Methanol and ethanol are the most preferable in terms of yield. These alcohols can be used individually or in combination.

The solvent can be the mixed solvent mainly composed of the alcohol. In the case of this mixed solvent, examples of other solvents combined with the alcohol are aromatic solvents such as benzene, toluene and xylene; ethereal solvents such as t-butyl methyl ether, ethylene glycol dimethyl ether and diethylene glycol dimethyl ether; hydrocarbon solvents such as hexane, heptane and cyclohexane; and halogenic solvents such as dichloromethane, chloroform and 1,2-dichloroethane.

Sodium borohydride to be used in the first process can be a commercially available product. When the starting material is the optically active or racemic malic diester, an amount of sodium borohydride is preferably 1.6 to 5.3 moles, more preferably 1.6 to 2.6 moles to one mole of the malic diester. When the amount of the reducing agent is less than 1.6 moles, the reaction is not completed, and the yield is liable to decrease. When the starting material is optically active or racemic 3-hydroxy-γ-butyrolactone or 3,4-dihydroxybutanoate, the amount of the reducing agent is preferably 0.8 to 2.6 moles, more preferably 0.8 to 1.3 moles to one mole of 3-hydroxy-γ-butyrolactone or the 3,4-dihydroxybutanoate. When the amount of the reducing agent is less than 0.8 mole, the reaction is not completed, and the yield is liable to decrease.

Examples of modes of the first process are i) a method wherein sodium borohydride is added to a solution of the malic diester, 3-hydroxy-γ-butyrolactone, the 3,4-dihydroxybutanoate or the mixture thereof, which is the starting material, in the alcohol or the mixed solvent containing the alcohol, ii) a method wherein sodium borohydride is suspended in a solvent which is inert on sodium borohydride, and the malic diester, 3-hydroxy-γ-butyrolactone, the 3,4-dihydroxybutanoate or the mixture thereof, which is the starting material, and the alcohol or the mixed solvent containing the alcohol are added (preferably dropwise) thereto separately or in the form of a solution wherein they are mixed, iii) a method wherein sodium borohydride and the malic diester, 3-hydroxy-γ-butyrolactone, the 3,4-dihydroxybutanoate or the mixture thereof, which is the starting material, are suspended in the solvent which is inert on sodium borohydride, and the alcohol or the mixed solvent containing the alcohol is added (preferably dropwise) thereto, and the like.

In the above-mentioned modes ii) and iii), the reaction can be carried out at a high concentration of sodium borohydride, so that the reaction is efficient, and these modes are more preferable. Furthermore, since the liquid is added dropwise to the suspension as mentioned above in the methods of these modes, operation is also simpler than that of the method wherein sodium borohydride, which is a solid, is added. An amount of the alcohol or the mixed solvent containing the alcohol to be used in these modes is preferably one to ten equivalents, more preferably one to five equivalents to sodium borohydride.

Examples of the organic solvent which is inert on sodium borohydride are aromatic solvents such as benzene, toluene and xylene; ethereal solvents such as t-butyl methyl ether, ethylene glycol dimethyl ether and diethylene glycol dimethyl ether; hydrocarbon solvents such as hexane, heptane and cyclohexane; and halogenic solvents such as dichloromethane, chloroform and 1,2-dichloroethane.

The organic solvent is preferably an alcohol having four or more carbon atoms, preferably four to ten carbon atoms. Examples of the alcohol are 1-butanol, 2-butanol and 2-methyl-2-propanol. These alcohols can be used individually or in combination.

Reaction temperature of the reduction by the first process is not limited to a particular range, and the temperature is preferably −20° to 80° C., more preferably 0° to 50° C. When the temperature is lower than this range, the reaction proceeds slowly, viscosity of a reaction liquid also increases, and stirring is liable to be difficult. When the temperature exceeds this range, the solvent reacts with sodium borohydride, and the yield tends to decrease. The reaction is usually carried out under ordinary pressure and can be carried out under elevated pressure, if necessary. Reaction time is adjusted depending on reaction temperature and reaction pressure.

Next, ethereal solvents are preferable as the organic solvent to be used in the second process. Ethylene glycol dimethyl ether, diethylene glycol dimethyl ether (diglyme), dioxane and mixtures thereof are preferable in terms of treatment as the ethereal solvents.

The reducing agents to be used in the second process are the boronic reducing agents represented by the general formula $M(BH_4)_n$ (wherein "M" is the metal atom other than sodium, and "n" is the integer which is equal to the valence of the metal M). Lithium borohydride, magnesium borohydride, calcium borohydride, aluminum borohydride, titanium borohydride and tin borohydride are preferable among them. These reducing agents can be used individually or in combination. Reducing agents prepared in situ from metal salts and sodium borohydride are preferable in terms of easy handling of the boronic reducing agents. The boronic reducing agents prepared from the metal salts and sodium borohydride can be mainly composed of reaction products $M(BH_4)_n$, and can contain residual unreacted metal salts and/or unreacted sodium borohydride. Examples of the boronic reducing agent prepared from the metal salt and sodium borohydride in this manner are reducing agent mixtures prepared in later Examples.

Metal halides are preferable as these metal salts. Examples of the metal of the metal salt are lithium, magnesium, calcium, aluminum, titanium and tin. These metal salts can be used individually or in combination.

When the starting material is the optically active or racemic malic diester in the second process, an amount of the reducing agent is preferably 1.75 to 5 moles, more preferably 1.75 to 3 moles in the form of $BH_4$ to one mole of the malic diester. When the amount of the reducing agent is less than 1.75 moles in the form of $BH_4$, the reaction is not completed, and the yield is liable to decrease. When the amount is more than 5 moles, the cost of preparation tends to increase. When the starting material is optically active or racemic 3-hydroxy-γ-butyrolactone or 3,4-dihydroxybutanoate, the amount of the reducing agent is preferably 1 to 5 moles, more preferably 1 to 2 moles in the form of $BH_4$ to one mole of 3-hydroxy-γ-butyrolactone or the 3,4-dihydroxybutanoate. When the amount of the reducing agent is less than 1 mole in the form of $BH_4$, the reaction is not completed, and the yield is liable to decrease. When the amount is more than 5 moles, the cost of preparation tends to increase.

Reaction temperature of the reduction by the second process is not limited to a particular range, and the temperature is preferably −20° to 30° C. The reaction is usually carried out under ordinary pressure and can be carried out under elevated pressure, if necessary. Reaction time is adjusted depending on reaction temperature and reaction pressure.

A third process according to the present invention is a process for preparing 1,2,4-butanetriol wherein a malic diester, 3-hydroxy-γ-butyrolactone or a 3,4-dihydroxybutanoate represented by the following formulae (I) or a mixture thereof as a starting material is reduced with sodium borohydride in a reaction medium to give 1,2,4-butanetriol represented by the following formula (II), characterized in that sodium borohydride contained in a first alcohol and the starting material contained in a second alcohol, which is different from the first alcohol, are provided for the reaction.

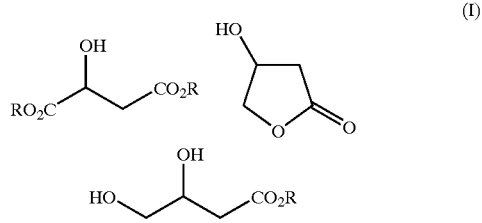

(I)

(wherein "R" is alkyl group having four carbon atoms or fewer).

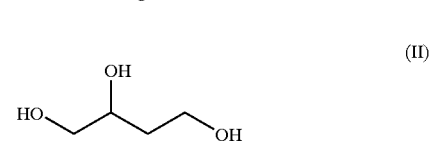

(II)

Specifically, the third process is a process for preparing 1,2,4-butanetriol characterized in that a first alcohol containing sodium borohydride is added to a solution containing a malic diester, 3-hydroxy-γ-butyrolactone or a 3,4-dihydroxybutanoate represented by the following formulae (I), or a mixture thereof as a starting material in a second alcohol, which is different from the first alcohol, or, the solution containing the starting material in a second alcohol is added to the first alcohol containing sodium borohydride, to reduce the starting material to give 1,2,4-butanetriol represented by the following formula (II)

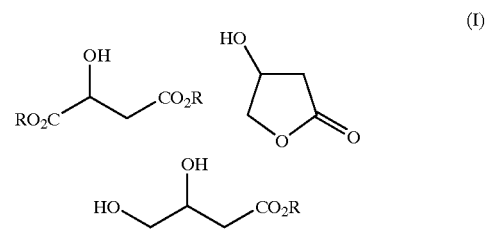

(I)

(wherein "R" is alkyl group having four carbon atoms or fewer).

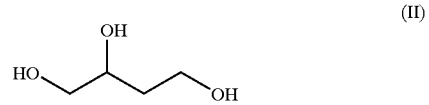

(II)

That is to say, the third process comprises following two methods:

(1) the first alcohol containing sodium borohydride is added to a solution containing the starting material in the second alcohol,
(2) the solution containing the starting material in the second alcohol is added to the first alcohol containing sodium borohydride.

In the third process, the malic diester, 3-hydroxy-γ-butyrolactone and the 3,4-dihydroxybutanoate can be optically active substances represented by the following formulae (III), and 1,2,4-butanetriol can be an optically active substance represented by the following formula (IV)

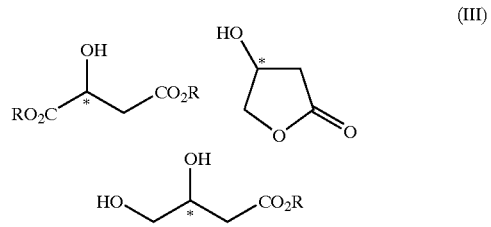

(III)

(wherein "R" is an alkyl group having four carbon atoms or fewer).

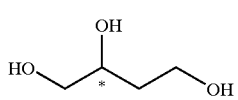
(IV)

In the third process, sodium borohydride is at least partially suspended in the first alcohol. The first alcohol is preferably an alcohol having four or more carbon atoms, preferably four to ten carbon atoms, and the second alcohol is preferably an alcohol having three or less carbon atoms. Examples of the first alcohol are 1-butanol, 2-butanol and 2-methyl-2-propanol, and Examples of the second alcohol are methanol and ethanol. These alcohols can be used individually or in combination.

An amount of the first alcohol is preferably 3 to 10 grams, more preferably 5 to 7 grams to one gram of sodium borohydride. An amount of the second alcohol is preferably 0.3 to 15 grams, more preferably 0.5 to 0.9 gram to one gram of the starting material.

An amount of sodium borohydride is preferably 1 to 5 moles, more preferably 1.5 to 1.8 moles to one mole of the starting material. When the amount of the reducing agent is too little, the reaction is not completed, and the yield is liable to decrease.

Reaction temperature of the reduction by the third process is preferably −20° to 80° C., more preferably 0° to 50° C. The reaction is usually carried out under ordinary pressure and can be carried out under elevated pressure, if necessary. Reaction time is adjusted depending on reaction temperature and reaction pressure.

In case where an ethereal solvent, especially THF is used in stead of the first alcohol as a medium suspending a part of or substantially the whole of sodium borohydride, the yield is only about 80%. Further, THF is dangerous in that it is apt to be oxidized in the air to produce an explosive peroxide. Accordingly, it is not preferable to use THF as a suspension medium of sodium borohydride.

In the first process to the third process, the object product is obtained by post-treating a reaction mixture with a mineral acid after the reaction, filtering out the resulting insoluble matter, evaporating an excess solvent under reduced pressure and adding a base to the resulting residue to neutralize it, or by treating the reaction mixture with an ion exchange resin and then carrying out usual purification such as distillation. Hydrogen chloride or sulfuric acid is preferable in terms of solubility of a salt in the solvent and easy handling of the mineral acid. Anion exchange resins, particularly basic anion exchange resins are preferable as the ion exchange, resin. Particularly preferred ion exchange resins are resins having an amino functional group. Examples of the ion exchange resin are basic anion exchange resins whose functional group is a dimethylamino group, a 1-deoxy-1-(methylamino)glycitol group or the like. Commercially available examples of such ion exchange resins are "XE-583", "IRA-743", "IRA-96SB" and "XT6050RF" manufactured by Organo Co., Ltd. and the like. Examples of the method of treating the reduction product with the ion exchange resin are a method wherein a liquid containing the product is flowed through a column filled with the ion exchange resin, a method wherein the ion exchange resin is put in the liquid containing the product and the whole is stirred, and the like. Residual boron or boron compounds can be removed by the ion exchange resin treatment. This makes it possible to inhibit polymeric by-products from forming when the product is purified later by distillation, and the yield increases.

The reduction product can be treated in the same manner as mentioned above with silica gel instead of the ion exchange resin. A high-purity object product can also be obtained by the silica gel treatment for the same reason as that of the ion exchange resin treatment.

BEST MODE FOR CARRYING OUT THE INVENTION

The present invention is described specifically by Examples hereinafter, but the present invention is not limited to these Examples.

EXAMPLE 1

Preparation of 1,2,4-butanetriol i) In 250 ml of ethanol was dissolved 38 g (0.20 mol) of diethyl malate, and 17.0 g (0.45 mol) of sodium borohydride was added thereto while keeping temperature at 20° C.

ii) This mixture was stirred at 20° C. for 15 hours and then cooled with ice. To the reaction mixture was added 100 ml of saturated HCl-EtOH, and then the resulting insoluble matter was filtered out. The filtrate was passed through a column filled with 100 g of an ion exchange resin ("XE-583" manufactured by Organo Co., Ltd.) to remove residual boron and then concentrated under reduced pressure. The concentrate was further purified by distillation to give 16.9 g (yield 79.7%) of 1,2,4-butanetriol.

EXAMPLE 2

Preparation of (S)-1,2,4-butanetriol i) In 250 ml of ethanol was dissolved 38 g (0.20 mol) of diethyl (S)-malate, and 17.0 g (0.45 mol) of sodium borohydride was added thereto while keeping temperature at 20° C.

ii) This mixture was stirred at 20° C. for 15 hours and then cooled with ice. To the reaction mixture was added 100 ml of saturated HCl-EtOH, and then the resulting insoluble matter was filtered out. The filtrate was passed through a column filled with 100 g of an ion exchange resin ("XE-583" manufactured by Organo Co., Ltd.) to remove residual boron and then concentrated under reduced pressure. The concentrate was further purified by distillation to give 17.2 g (yield 81.1%, 99.7% ee) of (S)-1,2,4-butanetriol.

EXAMPLE 3

Preparation of (S)-1,2,4-butanetriol

The same procedure as in Example 2 was repeated except that the ion exchange resin was replaced with "IRA-743" manufactured by Organo Co., Ltd. at the step ii) to give 16.7 g (yield 78.8%, 99.6% ee) of (S)-1,2,4-butanetriol.

EXAMPLE 4

Preparation of (S)-1,2,4-butanetriol

The same procedure as in Example 2 was repeated except that saturated HCl-EtOH was replaced with 15 ml (0.28 mol) of sulfuric acid at the step ii) to give 14.8 g (yield 74.5%, 99.7% ee) of (S)-1,2,4-butanetriol.

EXAMPLE 5

Preparation of (S)-1,2,4-butanetriol

The same procedure as in Example 2 was repeated except that the ion exchange resin was replaced with "IRA-96SB"

manufactured by Organo Co., Ltd. at the step ii) to give 15.8 g (yield 74.5%, 99.6% ee) of (S)-1,2,4-butanetriol.

EXAMPLE 6

Preparation of (R)-1,2,4-butanetriol

In 250 ml of a mixed solvent of ethanol:toluene=87:13 was dissolved 38 g (0.20 mol) of diethyl (R)-malate, and 17.0 g (0.45 mol) of sodium borohydride was added thereto while keeping temperature at 20° C.

Then, the same procedure as at the step ii) in Example 2 was repeated to give 16.9 g (yield 79.7%, 99.7% ee) of (R)-1,2,4-butanetriol.

EXAMPLE 7

Preparation of (R)-1,2,4-butanetriol

In 250 ml of a mixed solvent of ethanol:isopropanol=87:13 was dissolved 38 g (0.20 mol) of diethyl (R)-malate, and 17.0 g (0.45 mol) of sodium borohydride was added thereto while keeping temperature at 20° C.

Then, the same procedure as at the step ii) in Example 2 was repeated to give 16.5 g (yield 77.8%, 99.7% ee) of (R)-1,2,4-butanetriol.

EXAMPLE 8

Preparation of (S)-1,2,4-butanetriol

In 250 ml of ethylene glycol was dissolved 38 g (0.20 mol) of diethyl (S)-malate, and 17.0 g (0.45 mol) of sodium borohydride was added thereto while keeping temperature at 20° C.

Then, the same procedure as at the step ii) in Example 2 was repeated to give 15.1 g (yield 70.7%, 99.4% ee) of(S)-1,2,4-butanetriol.

EXAMPLE 9

Preparation of (S)-1,2,4-butanetriol

In 250 ml of propylene glycol was dissolved 38 g (0.20 mol) of diethyl (S)-malate, and 17.0 g (0.45 mol) of sodium borohydride was added thereto while keeping temperature at 20° C.

Then, the same procedure as at the step ii) in Example 2 was repeated to give 13.7 g (yield 64.6%, 99.5% ee) of (S)-1,2,4-butanetriol.

EXAMPLE 10

Preparation of (S)-1,2,4-butanetriol

In 250 ml of ethanol was dissolved 17.2 g (0.20 mol, 95.1% ee) of (S)-3-hydroxy-γ-butyrolactone, and 8.5 g (0.23 mol) of sodium borohydride was added thereto while keeping temperature at 20° C.

Then, the same procedure as at the step ii) in Example 2 was repeated to give 15.2 g (yield 71.7%, 94.8% ee) of (S)-1,2,4-butanetriol.

EXAMPLE 11

Preparation of (S)-1,2,4-butanetriol

In 250 ml of a mixed solvent of ethanol:toluene=87:13 was dissolved 17.2 g (0.20 mol, 95.1% ee) of (S)-3-hydroxy-γ-butyrolactone, and 8.5 g (0.23 mol) of sodium borohydride was added thereto while keeping temperature at 20° C.

Then, the same procedure as at the step ii) in Example 2 was repeated to give 14.8 g (yield 69.8%, 94.7% ee) of (S)-1,2,4-butanetriol.

EXAMPLE 12

Preparation of (R)-1,2,4-butanetriol

In 250 ml of ethanol was dissolved 29.6 g (0.20 mol, 94.4% ee) of ethyl (R)-3,4-dihydroxybutanoate, and 8.5 g (0.23 mol) of sodium borohydride was added thereto while keeping temperature at 20° C.

Then, the same procedure as at the step ii) in Example 2 was repeated to give 16.8 g (yield 79.2%, 94.1% ee) of (R)-1,2,4-butanetriol.

EXAMPLE 13

Preparation of (R)-1,2,4-butanetriol

In 250 ml of a mixed solvent of ethanol:toluene=87:13 was dissolved 29.6 g (0.20 mol, 94.4% ee) of ethyl (R)-3,4-dihydroxybutanoate, and 8.5 g (0.23 mol) of sodium borohydride was added thereto while keeping temperature at 20° C.

Then, the same procedure as at the step ii) in Example 2 was repeated to give 16.4 g (yield 77.4%, 94.2% ee) of (R)-1,2,4-butanetriol.

EXAMPLE 14

Preparation of (S)-1,2,4-butanetriol

In 200 ml of toluene was suspended 76 g (2 mol) of sodium borohydride, and 190 g (1 mol) of diethyl (S)-malate and 128 g (4 mol) of methanol were added dropwise thereto. The mixture was stirred at room temperature for six hours and then cooled with ice. Then, 220 ml of saturated HCl-MeOH was added thereto, and the resulting insoluble matter was filtered out. The filtrate was passed through a column filled with 100 g of an ion exchange resin ("XE-583" manufactured by Organo Co., Ltd.) to remove residual boron and then concentrated under reduced pressure. The concentrate was further purified by distillation to give 88 g (yield 83%, optical purity 99.7% ee) of (S)-1,2,4-butanetriol.

EXAMPLE 15

Preparation of (S)-1,2,4-butanetriol

In 200 ml of toluene was suspended 76 g (2 mol) of sodium borohydride, and 190 g (1 mol) of diethyl (S)-malate and 128 g (4 mol) of methanol were added dropwise thereto. The mixture was stirred at room temperature for six hours and then cooled with ice. To the reaction mixture was added 220 ml of saturated HCl-MeOH, and the resulting insoluble matter was filtered out. The filtrate was concentrated under reduced pressure, methanol was added thereto, and the mixture was concentrated under reduced pressure again. The concentrate was purified by distillation to give 85 g (yield 80%, optical purity 99.7% ee) of (S)-1,2,4-butanetriol.

EXAMPLE 16

Preparation of 1,2,4-butanetriol i) To 200 ml of 1,2-dimethoxyethane were added 15 g (0.40 mol) of sodium borohydride and 17 g (0.40 mol) of lithium chloride, and the mixture was stirred for three hours to prepare a solution containing a reducing agent mixture.

Then, 32 g (0.20 mol) of dimethyl malate was dissolved in 100 ml of 1,2-dimethoxyethane, and the solution was added dropwise to the solution containing the reducing agent mixture while keeping temperature at 10° to 20° C.

ii) This mixture was stirred at 20° C. for 15 hours and then cooled with ice. To the reaction mixture was added 100 ml of saturated HCl-MeOH, and then the resulting insoluble matter was filtered out. The filtrate was passed through a column filled with 100 g of an ion exchange resin ("XE-583" manufactured by Organo Co., Ltd.) to remove residual boron and then concentrated under reduced pressure. The concentrate was further purified by distillation to give 16.9 g (yield 78.8%) of 1,2,4-butanetriol.

EXAMPLE 17

Preparation of (S)-1,2,4-butanetriol i) To 200 ml of 1,2-dimethoxyethane were added 15 g (0.40 mol) of sodium borohydride and 17 g (0.40 mol) of lithium chloride, and the mixture was stirred for three hours to prepare a solution containing a reducing agent mixture. Then, 32 g (0.20 mol) of dimethyl (S)-malate was dissolved in 100 ml of 1,2-dimethoxyethane, and the solution was added dropwise to the solution containing the reducing agent mixture while keeping temperature at 10° to 20° C.

ii) This mixture was stirred at 20° C. for 15 hours and then cooled with ice. To the reaction mixture was added 100 ml of saturated HCl-MeOH, and then the resulting insoluble matter was filtered out. The filtrate was passed through a column filled with 100 g of an ion exchange resin ("XE-583" manufactured by Organo Co., Ltd.) to remove residual boron and then concentrated under reduced pressure. The concentrate was further purified by distillation to give 16.9 g (yield 80.7%, 99.4% ee) of (S)-1,2,4-butanetriol.

EXAMPLE 18

Preparation of (S)-1,2,4-butanetriol

To 200 ml of diglyme were added 15 g (0.40 mol) of sodium borohydride and 11.0 g (0.10 mol) of calcium chloride, and the mixture was stirred for 12 hours to prepare a solution containing a reducing agent mixture. Then, 32 g (0.20 mol) of dimethyl (S)-malate was dissolved in 100 ml of diglyme, and the solution was added dropwise to the solution containing the reducing agent mixture while keeping temperature at 10° to 20° C.

Then, the same procedure as at the step ii) in Example 17 was repeated to give 14.8 g (yield 70.7%, 99.5% ee) of (S)-1,2,4-butanetriol.

EXAMPLE 19

Preparation of (R)-1,2,4-butanetriol

To 200 ml of diglyme were added 15 g (0.40 mol) of sodium borohydride and 17.8 g (0.14 mol) of aluminum chloride, and the mixture was stirred for three hours to prepare a solution containing a reducing agent mixture. Then, 32 g (0.20 mol) of dimethyl (R)-malate was dissolved in 100 ml of diglyme, and the solution was added dropwise to the solution containing the reducing agent mixture while keeping temperature at 10° to 20° C.

Then, the same procedure as at the step ii) in Example 17 was repeated to give 15.5 g (yield 74.0%, 98.5% ee) of (R)-1,2,4-butanetriol.

EXAMPLE 20

Preparation of (S)-1,2,4-butanetriol

To 200 ml of diglyme were added 15 g (0.40 mol) of sodium borohydride and 19.0 g (0.10 mol) of titanium chloride, and the mixture was stirred for three hours to prepare a solution containing a reducing agent mixture. Then, 32 g (0.20 mol) of dimethyl (S)-malate was dissolved in 100 ml of diglyme, and the solution was added dropwise to the solution containing the reducing agent mixture while keeping temperature at 10° to 20° C.

Then, the same procedure as at the step ii) in Example 17 was repeated to give 14.9 g (yield 71.1%, 98.7% ee) of (S)-1,2,4-butanetriol.

EXAMPLE 21

Preparation of (S)-1,2,4-butanetriol

To 200 ml of 1,2-dimethoxyethane were added 7.6 g (0.20 mol) of sodium borohydride and 8.5 g (0.20 mol) of lithium chloride, and the mixture was stirred for three hours to prepare a solution containing a reducing agent mixture. Then, 17.2 g (0.20 mol, 95.1% ee) of (S)-3-hydroxy-γ-butyrolactone was dissolved in 100 ml of 1,2-dimethoxyethane, and the solution was added dropwise to the solution containing the reducing agent mixture while keeping temperature at 10° to 20° C.

Then, the same procedure as at the step ii) in Example 17 was repeated to give 15.7 g (yield 75.0%, 94.7% ee) of (S)-1,2,4-butanetriol.

EXAMPLE 22

Preparation of (S)-1,2,4-butanetriol

To 200 ml of 1,2-dimethoxyethane were added 7.6 g (0.20 mol) of sodium borohydride and 8.9 g (0.07 mol) of aluminum chloride, and the mixture was stirred for three hours to prepare a solution containing a reducing agent mixture. Then, 17.2 g (0.20 mol, 95.1% ee) of (S)-3-hydroxy-γ-butyrolactone was dissolved in 100 ml of 1,2-dimethoxyethane, and the solution was added dropwise to the solution containing the reducing agent mixture while keeping temperature at 10° to 20° C.

Then, the same procedure as at the step ii) in Example 17 was repeated to give 15.0 g (yield 71.6%, 94.2% ee) of (S)-1,2,4-butanetriol.

EXAMPLE 23

Preparation of (S)-1,2,4-butanetriol

To 200 ml of diglyme were added 7.6 g (0.20 mol) of sodium borohydride and 9.5 g (0.05 mol) of titanium chloride, and the mixture was stirred for three hours to prepare a solution containing a reducing agent mixture. Then, 17.2 g (0.20 mol, 95.1% ee) of (S)-3-hydroxy-γ-butyrolactone was dissolved in 100 ml of diglyme, and the solution was added dropwise to the solution containing the reducing agent mixture while keeping temperature at 10° to 20° C.

Then, the same procedure as at the step ii) in Example 17 was repeated to give 14.1 g (yield 67.3%, 94.4% ee) of (S)-1,2,4-butanetriol.

EXAMPLE 24

Preparation of (R)-1,2,4-butanetriol

To 200 ml of diglyme were added 9.5 g (0.25 mol) of sodium borohydride and 10.6 g (0.25 mol, 94.4% ee) of lithium chloride, and the mixture was stirred for three hours to prepare a solution containing a reducing agent mixture.

Then, 29.6 g (0.20 mol) of ethyl (R)-3,4-dihydroxybutanoate was dissolved in 100 ml of diglyme, and the solution was added dropwise to the solution containing the reducing agent mixture while keeping temperature at 10° to 20° C.

Then, the same procedure as at the step ii) in Example 17 was repeated to give 16.9 g (yield 80.4%, 93.9% ee) of (R)-1,2,4-butanetriol.

EXAMPLE 25

Preparation of (R)-1,2,4-butanetriol

To 200 ml of dioxane were added 9.5 g (0.25 mol) of sodium borohydride and 11.1 g (0.08 mol) of aluminum chloride, and the mixture was stirred for three hours to prepare a solution containing a reducing agent mixture. Then, 29.6 g (0.20 mol, 94.4% ee) of ethyl (R)-3,4-dihydroxybutanoate was dissolved in 100 ml of dioxane, and the solution was added dropwise to the solution containing the reducing agent mixture while keeping temperature at 10° to 20° C.

Then, the same procedure as at the step ii) in Example 17 was repeated to give 15.4 g (yield 73.5%, 93.0% ee) of (R)-1,2,4-butanetriol.

EXAMPLE 26

Preparation of (S)-1,2,4-butanetriol i) To 260 g of tert-butanol was added 41.5 g (1.1 mol) of sodium borohydride to form a suspension. A solution of 100 g (0.617 mol) of dimethyl (S)-malate in 78 g of methanol was added dropwise to the suspension.

ii) The obtained reaction mixture was stirred at 70° C. for five hours, and 120 ml of a 35% aqueous HCl solution was added to the reaction mixture. The resulting insoluble matters were filtered out. 1600 L of methanol was added to the filtrate and boron was removed by distilling methanol under an acidic condition. The obtained product was purified by distillation under reduced pressure to give 59.2 g (0.558 mol) of (S)-1,2,4-butanetriol (yield: 90.4%, optical purity: 99.1% ee).

EXAMPLE 27

Preparation of (S)-1,2,4-butanetriol

The reaction mixture obtained in the same manner as step (i) of Example 26 was stirred at 70° C. for five hours, and 120 ml of a 35% aqueous HCl solution was added to the reaction mixture.

Then the resulting insoluble matter was filtered out. The filtrate was passed through a column filled with 200 g of an ion exchange resin ("XE-583" manufactured by Organo Co., Ltd.) to remove residual boron and then concentrated under reduced pressure. The concentrate was further purified by distillation to give 58.6 g (yield 89.5%, 99.0% ee) of (S)-1,2,4-butanetriol.

EXAMPLE 28

Preparation of (S)-1,2,4-butanetriol

To 260 g of sec-butanol was added 41.5 g (1.1 mol) of sodium borohydride to form a suspension. A solution of 100 g (0.617 mol) of dimethyl (S)-malate in 78 g of methanol was added dropwise to the suspension.

Then, the same procedure as at the step ii) in Example 26 was repeated to give 58.3 g (0.549 mol) of (S)-1,2,4-butanetriol (yield: 89.0%, optical purity: 99.3% ee).

EXAMPLE 29

Preparation of (S)-1,2,4-butanetriol

A suspension of 41.5 g (1.1 mol) of sodium borohydride in 260 g of sec-butanol was added dropwise to a solution of 100 g (0.617 mol) of dimethyl (S)-malate in 78 g of methanol.

Then, the same procedure as at the step ii) in Example 26 was repeated to give 58.6 g (0.552 mol) of (S)-1,2,4-butanetriol (yield: 89.5%, optical purity: 99.0% ee).

EXAMPLE 30

Preparation of (S)-1,2,4-butanetriol

A suspension of 41.5 g (1.1 mol) of sodium borohydride in 260 g of tert-butanol was added dropwise to a solution of 100 g (0.617 mol) of dimethyl (S)-malate in 78 g of methanol.

Then, the same procedure as at the step ii) in Example 26 was repeated to give 58.9 g (0.555 mol) of (S)-1,2,4-butanetriol (yield: 90.0%, optical purity: 99.0% ee).

COMPARATIVE EXAMPLE 1

Use of Ethanol as a Solvent i) In 260 g of ethanol was dissolved 100 g (0.617 mol) of dimethyl (S)-malate, and 41.5 g (1.1 mol) of sodium borohydride was added thereto while keeping temperature at 20° C.

ii) The obtained reaction mixture was stirred at 20° C. for 15 hours and then cooled. To the reaction mixture was added 200 ml of saturated HCl-EtOH, and then the resulting insoluble matter was filtered out. The filtrate was passed through a column filled with 200 g of an ion exchange resin ("XE-583" manufactured by Organo Co., Ltd.) to remove residual boron and then concentrated under reduced pressure. The concentrate was further purified by distillation to give 42.6 g (yield 65.0%, 99.0% ee) of (s)-1,2,4-butanetriol.

COMPARATIVE EXAMPLE 2

Use of Toluene and Ethanol as a Solvent i) To 260 g of toluene was added 41.5 g (1.1 mol) of sodium borohydride, and a solution of 100 g (0.617 mol) of dimethyl (S)-malate in 78 g of methanol was added dropwise thereto.

ii) The obtained reaction mixture was stirred at 20 ° C. for six hours and then cooled. Then, 200 ml of saturated HCl-EtOH was added thereto, and the resulting insoluble matter was filtered out. The filtrate was passed through a column filled with 200 g of an ion exchange resin ("XE-583" manufactured by Organo Co., Ltd.) to remove residual boron and then concentrated under reduced pressure. The concentrate was further purified by distillation to give 45.9 g (yield 70.2%, optical purity 99.0% ee) of (S)-1,2,4-butanetriol.

Industrial Applicability

A process for preparation according to the present invention is a process wherein 1,2,4-butanetriol, which is a useful compound as a synthetic intermediate of medicines, agricultural chemicals and the like, can be obtained safely, easily and inexpensively without causing problems concerning wastewater, and a process which can advantageously be applied to industry.

What is claimed is:

1. A process for preparing 1,2,4-butanetriol characterized in that a malic diester represented by the following formula (I) is reduced with sodium borohydride with no other metal salt present in a first alcohol to give 1,2,4-butanetriol represented by the following formula (II)

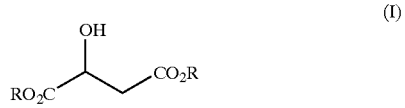

(wherein "R" is an alkyl group having four carbon atoms or fewer):

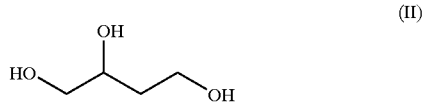

wherein the first alcohol is inert on sodium borohydride, and the malic diester and a second alcohol or a mixed solvent containing the second alcohol are added thereto.

2. A process for preparing 1,2,4-butanetriol characterized in that an optically active malic diester, 3-hydroxy-γ-butyrolactone or a 3,4-dihydroxybutanoate represented by the following formulae (III) or a mixture thereof is reduced with sodium borohydride with no other metal salt present in a first alcohol which is different from the first alcohol, to give optically active 1,2,4-butanetriol represented by the following formula (IV)

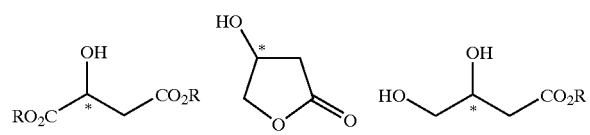

(wherein "R" is an alkyl group having four carbon atoms or fewer):

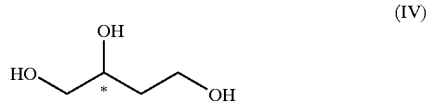

wherein the first alcohol is inert on sodium borohydride, and the optically active malic diester, 3-hydroxy-γ-butyrolactone, the 3,4-dihydroxybutanoate or a mixture thereof and a second alcohol which is different from the first alcohol, or a mixed solvent containing the second alcohol are added thereto.

3. A process for preparing 1,2,4-butanetriol as claimed in claim 1 or 2, wherein the first alcohol has four carbon atoms or more.

4. A process for preparing 1,2,4-butanetriol as claimed in claim 1 or 2, wherein sodium borohydride is at least partially suspended in the first alcohol.

5. A process for preparing 1,2,4-butanetriol as claimed in claim 1 or 2, wherein an amount of the first alcohol is one to five moles to one mole of sodium borohydride.

6. A process for preparing 1,2,4-butanetriol as claimed in claim 1 or 2, wherein the second alcohol has three carbon atoms or fewer.

7. A process for preparing 1,2,4-butanetriol as claimed in claim 6, wherein the second alcohol is methanol, ethanol, propanol, isopropanol, ethylene glycol, propylene glycol or a mixture thereof.

8. A process for preparing 1,2,4-butanetriol as claimed in claim 7, wherein the second alcohol is methanol and/or ethanol.

9. A process for preparing 1,2,4-butanetriol characterized in that a malic diester represented by the following formula (I) is reduced with a boronic reducing agent represented by the general formula $M(BH_4)_n$ (wherein "M" is a metal atom, and "n" is an integer which is equal to a valence of the metal M: wherein the boronic reducing agent is prepared from a corresponding metal salt and sodium borohydride and wherein the metal is selected from lithium, magnesium, calcium, aluminum, titanium and tin) in an organic solvent to give 1,2,4-butanetriol represented by the following formula (II)

(wherein "R" is an alkyl group having four carbon atoms or fewer)

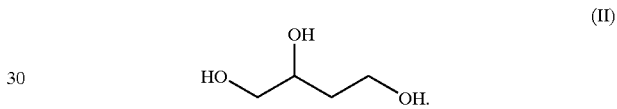

10. A process for preparing 1,2,4-butanetriol, characterized in that an optically active malic diester, 3-hydroxy-γ-butyrolactone or a 3,4-dihydroxybutanoate represented by the following formulae (III) or a mixture thereof is reduced with a boronic reducing agent represented by the general formula $M(BH_4)_n$ (wherein "M" is a metal atom, and "n" is an integer which is equal to a valence of the metal M: wherein the boronic reducing agent is prepared from a corresponding metal salt and sodium borohydride and wherein the metal is selected from lithium, magnesium, calcium, aluminum, titanium and tin) in an organic solvent to give optically active 1,2,4-butanetriol represented by the following formula (IV)

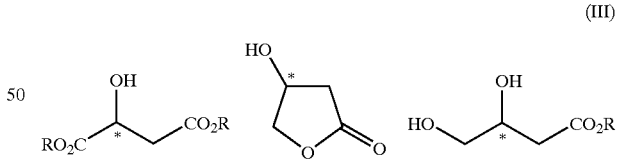

(wherein "R" is an alkyl group having four carbon atoms or fewer)

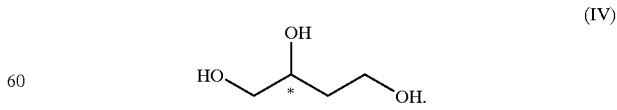

11. A process for preparing 1,2,4-butanetriol as claimed in claim 9 or 10, wherein the metal salt is a metal halide.

12. A process for preparing 1,2,4-butanetriol as claimed in any one of claim 9 or 10, wherein the organic solvent is an ethereal solvent.

13. A process for preparing 1,2,4-butanetriol as claimed in claim 12, wherein the ethereal solvent is ethylene glycol dimethyl ether, diethylene glycol dimethyl ether, dioxane or a mixture thereof.

14. A process for preparing 1,2,4-butanetriol as claimed in claim 1 or 9, wherein the resulting 1,2,4-butanetriol is purified with an ion exchange resin after the reduction.

15. A process for preparing 1,2,4-butanetriol as claimed in claim 14, wherein the ion exchange resin is an anion exchange resin.

16. A process for preparing 1,2,4-butanetriol as claimed in claim 15, wherein the anion exchange resin has an amino functional group.

17. A process for preparing 1,2,4-butanetriol as claimed in claim 1 or 9, wherein the resulting 1,2,4-butanetriol is purified with silica gel after the reduction.

18. A process for preparing 1,2,4-butanetriol wherein a malic diester, 3-hydroxy-γ-butyrolactone or a 3,4-dihydroxybutanoate represented by the following formulae (I) or a mixture thereof as a starting material is reduced with sodium borohydride in a reaction medium to give 1,2,4-butanetriol represented by the following formula (II), characterized in that sodium borohydride contained in a first alcohol and the starting material contained in a second alcohol, which is different from the first alcohol, are provided for the reaction.

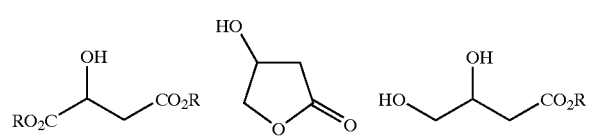
(I)

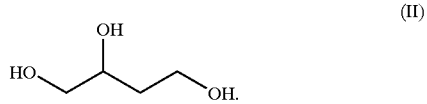
(II)

(wherein "R" is alkyl group having four carbon atoms or fewer).

19. A process for preparing 1,2,4-butanetriol characterized in that a first alcohol containing sodium borohydride is added to a solution containing a malic diester, 3-hydroxy-γ-butyrolactone or a 3,4-dihydroxybutanoate represented by the following formulae (I), or a mixture thereof as a starting material in a second alcohol, which is different from the first alcohol, or, the solution containing the starting material in a second alcohol is added to the first alcohol containing sodium borohydride, to reduce the starting material to give 1,2,4-butanetriol represented by the following formula (II)

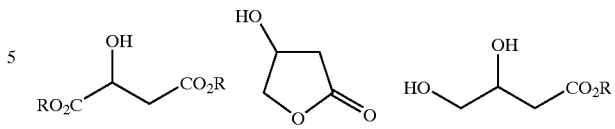
(I)

(wherein "R" is alkyl group having four carbon atoms or fewer).

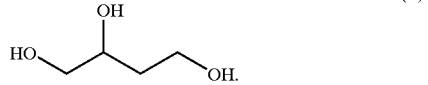
(II)

20. A process for preparing 1,2,4-butanetriol as claimed in claim 18, wherein the malic diester, 3-hydroxy-γ-butyrolactone and the 3,4-dihydroxybutanoate are optically active substances represented by the following formulae (III), and 1,2,4-butanetriol is an optically active substance represented by the following formula (IV)

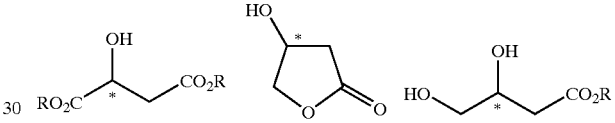
(III)

(wherein "R" is an alkyl group having four carbon atoms or fewer)

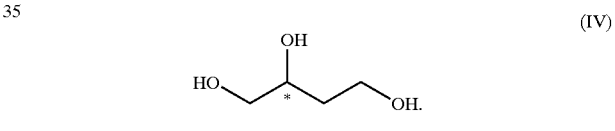
(IV)

21. A process for preparing 1,2,4-butanetriol as claimed in any one of claim 18 to 20, characterized in that sodium borohydride is at least partially suspended in the first alcohol.

22. A process for preparing 1,2,4-butanetriol as claimed in any one of claim 18 to 20, characterized in that the first alcohol is an alcohol having four or more carbon atoms, and the second alcohol is an alcohol having three or less carbon atoms.

23. A process for preparing 1,2,4-butanetriol as claimed in claim 22, characterized in that the first alcohol is 1-butanol, 2-butanol, 2-methyl-2-propanol or a mixture thereof, and the second alcohol is methanol, ethanol or a mixture thereof.

* * * * *